United States Patent [19]

Blau et al.

[11] 4,363,793

[45] Dec. 14, 1982

[54] DIAGNOSTIC RADIOPHARMACEUTICALS FOR LOCALIZATION IN TARGET TISSUES EXHIBITING A REGIONAL PH SHIFT RELATIVE TO SURROUNDING TISSUES

[75] Inventors: Monte Blau, Buffalo; Hank F. Kung, Amherst, both of N.Y.

[73] Assignee: State University of New York, Albany, N.Y.

[21] Appl. No.: 174,491

[22] Filed: Aug. 8, 1980

Related U.S. Application Data

[63] Continuation-in-part of Ser. No. 71,189, Aug. 30, 1979, abandoned.

[51] Int. Cl.³ .................... A61K 49/00; A61K 43/00
[52] U.S. Cl. .......................................... 424/1; 424/9;
424/248.4; 424/256; 424/325
[58] Field of Search ............... 424/1, 9, 246, 248.4, 424/256, 325

[56] References Cited

U.S. PATENT DOCUMENTS

| | | | |
|---|---|---|---|
| 3,961,038 | 6/1976 | Benes | 424/1 |
| 3,995,020 | 11/1976 | Dandamudi | 424/1 |
| 4,011,307 | 3/1977 | Lambrecht et al. | 424/1 |
| 4,083,947 | 4/1978 | Monks et al. | 424/9 |
| 4,202,876 | 5/1980 | Monks et al. | 424/9 |
| 4,215,045 | 7/1980 | Knapp, Jr. | 424/1 |

OTHER PUBLICATIONS

Heindel et al., Ed., *The Chemistry of Radio Pharmaceuticals,* Masson Publishing USA, Inc., New York, 1978, p. 43.
Anghileri, from *Principles of Radiopharmacology,* vol. III, Colombetti, Ed, CRC Press, Inc., 1979, pp. 243–258.

*Primary Examiner*—Christine M. Nucker
*Attorney, Agent, or Firm*—Michael L. Dunn

[57] ABSTRACT

A radiopharmaceutical chemical compound comprising a radioactive isotope, other than an isotope of iodine, in chemical combination with at least one amine group. The compound has a lipophilicity sufficiently high at a pH of 7.6 to permit passage of the compound from the blood of a mammal into a target organ or tissue and sufficiently low at a pH of 6.6 to prevent rapid return of the compound from the target organ or tissue to the blood. The compound has a percent protein binding of less than ninety percent.

A method for selectively depositing a radiopharmaceutical compound in at least one target tissue or organ of a mammal, which tissue or organ has a significantly different intracellular pH than the blood of the mammal, by introducing the compound of the invention into the bloodstream of the mammal.

21 Claims, 3 Drawing Figures

FIG. 1

DIAGNOSTIC RADIOPHARMACEUTICALS FOR LOCALIZATION IN TARGET TISSUES EXHIBITING A REGIONAL PH SHIFT RELATIVE TO SURROUNDING TISSUES

This is a continuation-in-part of co-pending patent application Ser. No. 071,189 filed Aug. 30, 1979 entitled DIAGNOSTIC RADIOPHARMACEUTICALS FOR LOCALIZATION IN TARGET TISSUES EXHIBITING A REGIONAL PH SHIFT RELATIVE TO SURROUNDING TISSUES now abandoned.

BACKGROUND OF THE INVENTION (A) Field of the Invention

The present invention is directed to a method for selectively depositing for diagnostic purposes radiopharmaceutical compounds in target tissues or organs of a mammal. Mammal as used herein includes the human being. The invention more particularly relates to radiopharmaceutical compounds which are capable of selective accumulation in tissues or organs having lowered intracellular pH as a result of normal metabolism or diseased state.

(B) Description of the Prior Art

Radiopharmaceutical compounds have been in use for diagnostic purposes for a long time. Those well versed in the art relating to radiopharmaceuticals and nuclear medicine are well aware of the requirements which must be satisfied by a diagnostically useful radiopharmaceutical compound. Briefly, these requirements include the following. The radiopharmaceutical compound must be able to penetrate into a target tissue of organ and attain a sufficiently high concentration therein so that its presence is detectable by state of the art radiation monitoring means. The accumulation of the radiopharmaceutical compound in the target tissue or organ must be sufficiently selective relative to other tissues and organs of the body so that a diagnostic distinction for its presence in the target tissue or organ relative to the other tissues or organs can be made. Furthermore, the radiopharmaceutical compound must emit radiation capable of penetrating through several other tissues or organs of the body. Experience has shown that only radiopharmaceutical compounds emitting $\gamma$, X-ray or positron radiation satisfy this requirement. Finally, and preferably, a diagnostic radiopharmaceutical compound should be easily prepared from inexpensive and available radionuclides.

In order to gain the desired tissue or organ penetration and uptake specificity for a radiopharmaceutical compound, various physiological processes and phenomena have been exploited in the past. For example, radioactive compounds which are excreted or detoxified by the liver or kidney may accumulate in these organs long enough for permitting a diagnosis of liver or kidney malfunctions. Other radiopharmaceutical compounds may depend on a selective transport mechanism through the cell membranes for entry into the cells of the target tissue or organ. An example of such a compound is F-18 2-fluoro-2-deoxyglucose which, being a close structural analog of the ubiquitous metabolite glucose, enters cells through the existing active transport mechanism for glucose. Once inside the cell, F-18 2-fluoro-2-deoxyglucose undergoes phosphorylation to yield the corresponding 6-phosphate. F-18 2-fluoro-2-deoxyglucose 6-phosphate, however, does not enter the conventional metabolic pathways of glucose 6-phosphate and due to its state of ionization, is incapable of rapidly exiting from the cells by passive diffusion through the cell membranes. Consequently, it is effectively trapped within the cells. F-18 2-fluoro-2-deoxy-glucose, by mimicking the natural metabolite glucose, is capable of crossing the blood brain barrier and therefore has been found suitable for radiopharmaceutical mapping of the brain. The structures of radiopharmaceutical compounds, depending upon selective transport mechanisms, are obviously very limited since the cell must recognize the structure of the compound as being desirable for the cell.

Another example of a radiopharmaceutical compound which freely crosses cell membranes and thereafter is rather effectively trapped within the cells is N-13 labeled ammonia. After entry into the cells, N-13 labeled ammonia is enzymatically converted into amino acids and other metabolites which are incapable of diffusing out of the cell. For a detailed description of the biodistribution and metabolism of F-18 2-fluoro-2-deoxy-glucose and N-13 labeled ammonia reference is made to the following publications:

Gallagher B. M., Fowler J. S., Gutterson N. I., et al: Metabolic Trapping as a Principle of Radiopharmaceutical Design: Some Factors Responsible for the Biodistribution of ($^{18}$F) 2-deoxy-2-fluoro-D-glucose, J. Nucl Med 19:1154–1161, 1978; Phelps M. E., Hoffman E. J., Rayband C.: Factors which Affect Cerebral Uptake and Retention of $^{13}$NH$_3$, Stroke 8: 694–701, 1977; Gallagher B. M., Ansari A., Atkins H., et al: Radiopharmaceuticals XXVI. $^{18}$F-labeled 2-deoxy-2fluoro-D-glucose as a Radiopharmaceutical for Measuring Regional Myocardial Glucose Metabolism in vivo: Tissue Distribution and Imaging Studies in Animals, J Nucl Med 18: 990–996, 1977; Carter C. C., Lifton J. F., Welch M. J.: Oxygen Uptake and Blood pH and Concentration Effects of Ammonia in Dogs Determined with Ammonia Labeled with 10 Minutes Half-lived Nitrogen-13, Neurology 23: 204–213, 1973; Phelps M. E., Hoffman E. J., Selin C., et al: Investigation of ($^{18}$F) 2-fluoro-2-deoxy-glucose for the Measure of Myocardial Glucose Metabolism, J. Nuc. Med. 19: 1311–1319; Tewson T. J., Welch M. J., Raichle M. E.: ($^{18}$F)-Labeled 3-deoxy-3-fluoro-D-glucose: Synthesis and Preliminary Biodistribution Data, J. Nuc. Med. 19: 1339–1345.

In the above cited article authored by Phelps et al, Stroke 8: 694–701, 1977, it was recognized that ammonia is capable of penetrating the blood brain barrier only in the form of free ammonia (NH$_3$) and not as ammonium ion. Furthermore, this article has reiterated the teachings of the prior art that a strong correlation exists between lipid solubility characteristics of a compound, as measured by oil-water partition coefficients, and the blood brain barrier penetration capability of the compound. A significant disadvantage of radiopharmaceuticals bearing F-18 labeled fluorine or N-13 labeled nitrogen is that these radionuclides are not generally available.

Other radiopharmaceutical compounds have been designed which take advantage of lipid solubility to permit the compound to enter the organ or tissue. See e.g. Michael D. Loberg et al: Membrane Transport of Tc-99m-Labeled Radiopharmaceuticals. I. Brain Uptake by Passive Transport: J. Nucl. Med. Vol. 20, No. 11, pp 1181–1188. Most of the compounds described in the Loberg et al article nevertheless have ionic substituents and have no means for enhancing their retention within the cellular structure of the organ or tissue.

Other such compounds use various isotopes of iodine as the radioactive component (radionuclide) of the radiopharmaceutical compound. Some of such iodine containing compounds are believed to have taken advantage of lipid solubility in order to enter the cell and, although not recognized in the prior art, some may have even inherently been held within an organ or tissue due to a drop in pH. An example of such a prior art iodine containing compound which may have such previously unrecognized properties is 1,4,-(di methylamino)-methyl-3-iodobenzene. Unfortunately the most desirable isotope of iodine, $^{123}$I, is not readily available. Furthermore, radioactive iodine is known to accumulate in the thyroid which is undesirable. Therefore when isotopes of iodine are used additional medical method steps are required to reduce or prevent such accumulations.

As was briefly pointed out above, the prior art has designed several radiopharmaceutical compounds which exploit various differents in metabolic or physiological states of the several tissues of the body for diagnostic purposes. The prior art, however, has not yet knowingly designed or recognized that radiopharmaceutical compounds could be designed which utilize differences between the pH of the blood and the intracellular pH of various organs or tissues to retain the compound within the organ or tissue. This is true in spite of the fact that the brain, as well as several actively metabolizing tissues such as the heart and some tumors, have been known to possess a lower intracellular pH than the blood stream. Furthermore, regional pH differences within an organ have been shown to exist due to local ischemia or other abnormal metabolic states. The relative difference between the intracellular pH of certain tissues or organs of the body compared to other tissues, organs or the bloodstream is termed for the purposes of the present description, regional pH shift.

For a detailed discussion of the intracellular pH and regional pH shift within the various organs and tissues of the human body, reference is made to an article by W. J. Waddell and R. G. Bates titled "Intracellular pH", Physiological Review 49: 286–329, 1969.

SUMMARY OF THE INVENTION

In accordance with the present invention, diagnostic radiopharmaceutical compounds are provided which are capable of entering a target tissue or a target organ by passive diffusion through cell walls and which are effectively accumulated and retained within the target tissue or organ due to a regional pH shift. Such compounds are desirably readily accessible synthetically using readily available radionuclides other than iodine.

More specifically, the radiopharmaceutical compound comprises a radioactive isotope of an element in chemical combination with at least one amine group and preferably with at least two secondary or tertiary amine groups. The radioactive element is an element, other than iodine, emitting gamma ray ($\gamma$-ray), X-ray or positron radiation which is detectable or observable by state of the art radiation detecting means. Desirably, when the element is a gamma ray emitting isotope, at least seventy-five percent of the number of emissions are emitted at energies of between 80 and 400 kiloelectron volts and preferably between 80 and 300 kiloelectron volts. The half-life of the isotope is usually between 2 minutes and 15 days and often between 15 minutes and 3 days. Unless the isotope can be easily and almost completely eliminated by the mammals being tested, isotopes with long lives are usually avoided to prevent excessive radiation exposure. Isotopes with very short lives are often not used because of the practical problems encountered with time delays due to transporting the isotope, making the compound and completing the test before the isotope excessively decays.

In general, the compound has acid-base characteristics such that the state of ionization of the compound at the pH of the blood of the mammal is significantly different and usually less than its state of ionization at the intracellular pH of the target tissue or organ. The compound has such lipid solubility characteristics that the compound is capable of ready penetration through the cell walls of the target tissue or organ wherein due to a change in its state of ionization, its lipid solubility is substantially decreased whereby an ability of the compound to exit from the target tissue or organ is substantially diminished so that the compound is at least temporarily trapped within the target organ or tissue.

The compound desirably has a lipophilicity sufficiently high at a pH of 7.6 or higher and usually at a pH of 7.4 or higher to permit passage of the compound from the blood of a mammal into a target organ or tissue having a significantly different and usually lower intracellular pH than the blood of the mammal. The lipophilicity is sufficiently low at a pH of 6.6 or lower and usually at 7.0 or lower to prevent rapid return of the compound from the target organ or tissue to the blood. The compounds of the invention preferably have a percent protein binding of less than ninety percent. The compounds further preferably have no overall net positive charge at pH 12 and no net overall negative charge at pH 6.0. The compounds desirably have an octanol-aqueous medium partition coefficient which is significantly dependent on the pH of the aqueous medium at least in the pH range of 6.60 to 7.60.

In the method of the invention, the compounds are introduced into the blood circulation of a mammal, which as previously mentioned includes human beings, wherein they are in a relatively lipid soluble state. The compounds readily penetrate several tissues and organs of the body by passive diffusion. In target tissues or organs of the body wherein the intracellular pH is significantly lower than the pH of the blood stream, the compounds assume a more hydrophilic, less lipid soluble state whereby the rate of egress of the compounds from the cells by diffusion is significantly diminished. As a result, the compounds are at least temporarily trapped within the target tissue or organ and may be detected therein by the radiation monitoring means.

DETAILED DESCRIPTION OF THE INVENTION

In accordance with the present invention, radioactively labeled chemical compounds which preferentially accumulate in certain target tissues or organs of the body are prepared and introduced into the bloodstream of a mammal, including a human being. The target tissues or organs of the body, in accordance with the present invention, are tissues or organs which show a regional pH shift relative to surrounding tissues, organs or the bloodstream. As it was briefly discussed above, medical science has established that such regional pH shifts exist in the brain as well as in certain tumors and in ischemic heart tissue. Such pH shifts may also occur in various forms of abscesses. Since tumors may be entirely surrounded by healthy tissue of an organ, regional pH shifts may exist between healthy and malignant tissues of the same organ. The diagnostic significance of preferential accumulation of a radiopharmaceutical compound in a selected target organ or within the abnormal tissue of an organ is readily apparent to those skilled in the medical arts, and need not be further elaborated here.

Monitoring or observing the selective accumulation of radiopharmaceutical compounds in the target tissues or organs may be readily accomplished by currently available radioactive imaging or scanning techniques and instruments. The amount of radioactive labeled compound or radiopharmaceutical absorbed within the selected target tissue or organ may be expressed in terms of percentage of a total dose of the radiopharmaceutical compound which is injected into the animal.

Radiopharmaceutical compounds which may be used in the novel diagnostic method of the present invention must satisfy the following requirements. They must possess lipid solubility characteristics significantly dependent on pH in at least the 6.6 to 7.6 pH range and desirably in the 7.0 to 7.4 pH range. Since the regional pH shift in all of the presently known target organs or tissues is toward a pH lower than the normal pH of the blood (approximately 7.4), the compounds of the present invention must show increasing lipid solubility and therefore increasing cell wall penetrating capability with increasing pH, at least in the 6.60 to 7.60 pH range. In addition, the compounds of the present invention must also emit $\gamma$, X-ray or positron radiation which can penetrate through surrounding organs and tissues of the body for ultimate detection by suitable monitoring instruments. Most such desirable compounds emit $\gamma$ or positron radiation.

It is an important aspect of the present invention that the herein described radiopharmaceutical compounds penetrate through the cell walls by passive diffusion rather than being dependent on a specialized active or facilitated transport mechanism. The advantage of the ability to penetrate into the cells by diffusion is that the selective accumulation of a radiopharmaceutical compound of the present invention is principally dependent on the intracellular pH of the target, rather than on a close structural similarity to a metabolite for which an active or facilitated transport mechanism exists. As is well known in the biochemical and related arts, the requirement for structural similarity between an analog and a metabolite are very exacting for the analog to be actively transported into the cells. Thus, compounds of the present invention may be of a wide variety of chemical structures; the principal limiting requirement being the presence of the requisite lipid solubility-pH dependence characteristics. After having penetrated the target having a regional pH shift, the compound is effectively trapped in the cells of the target because it is less lipid soluble at the pH of the target than at the pH of the blood. Consequently, a rate of egress of the compound by passive diffusion from the target is significantly slower than its rate of entry, i.e., the rapid return of the compound to the blood is prevented, which results in accumulation of the compound in the target, e.g., the egress or return rate may be from 2 to more than 100 times slower than the entry rate and is thus relatively less rapid than the entry rate. To "prevent rapid return" as used throughout the specification and claims is relative and means that the relative rate of return to the blood from the organ or tissue is slower than the entry into the organ or tissue from the blood as previously discussed.

It has been found that conventional n-octanol-aqueous medium partition coefficients at several pH values of the aqueous medium provide excellent indicia to determine the sufficient lipophilicity of a radiopharmaceutical compound at pH 7.6 to permit passage of the compound from the blood into the target organ or tissue and the insufficient lipophilicity to prevent rapid return of the compound from the target organ or tissue to the blood at pH 6.6. The n-octanol-aqueous medium partition coefficients of the compound are readily measured in accordance with standard practice in the prior art. Briefly, such measurements include the steps of dissolving a known amount of the compound in an aqueous buffer of a predetermined pH and extracting the buffer solution with a known amount of n-octanol until an equilibrium of distribution of the compound between the aqueous and n-octanol phases occurs. The concentration of the compound in both phases is then measured by suitable analytical means, such as ultraviolet spectrophotometry; the partition coefficient being the ratio of the two measured concentrations.

For the purposes of evaluating a plurality of radioactive compounds for use in the novel method of the present invention, the n-octanol-aqueous medium partition coefficients of the compounds were measured in the following manner. The radioactive compound was mixed with 1.0 ml of n-octanol and 1.0 ml of buffer of the desired predetermined pH. The radioactivity of this mixture was counted, and the mixture was placed in a water bath shaker at 37° C. for 2 hours. After centrifugation at 3,000 rpm for 5 minutes, the n-octanol layer was separated and its radioactivity counted. The partition coefficient of the compound was calculated by the following equation:

$$\text{Partition Coefficient} = \frac{\text{counts in n-octanol}}{\text{initial counts} - \text{counts in n-octanol}} \quad \text{(Equation 1)}$$

Figure 1:
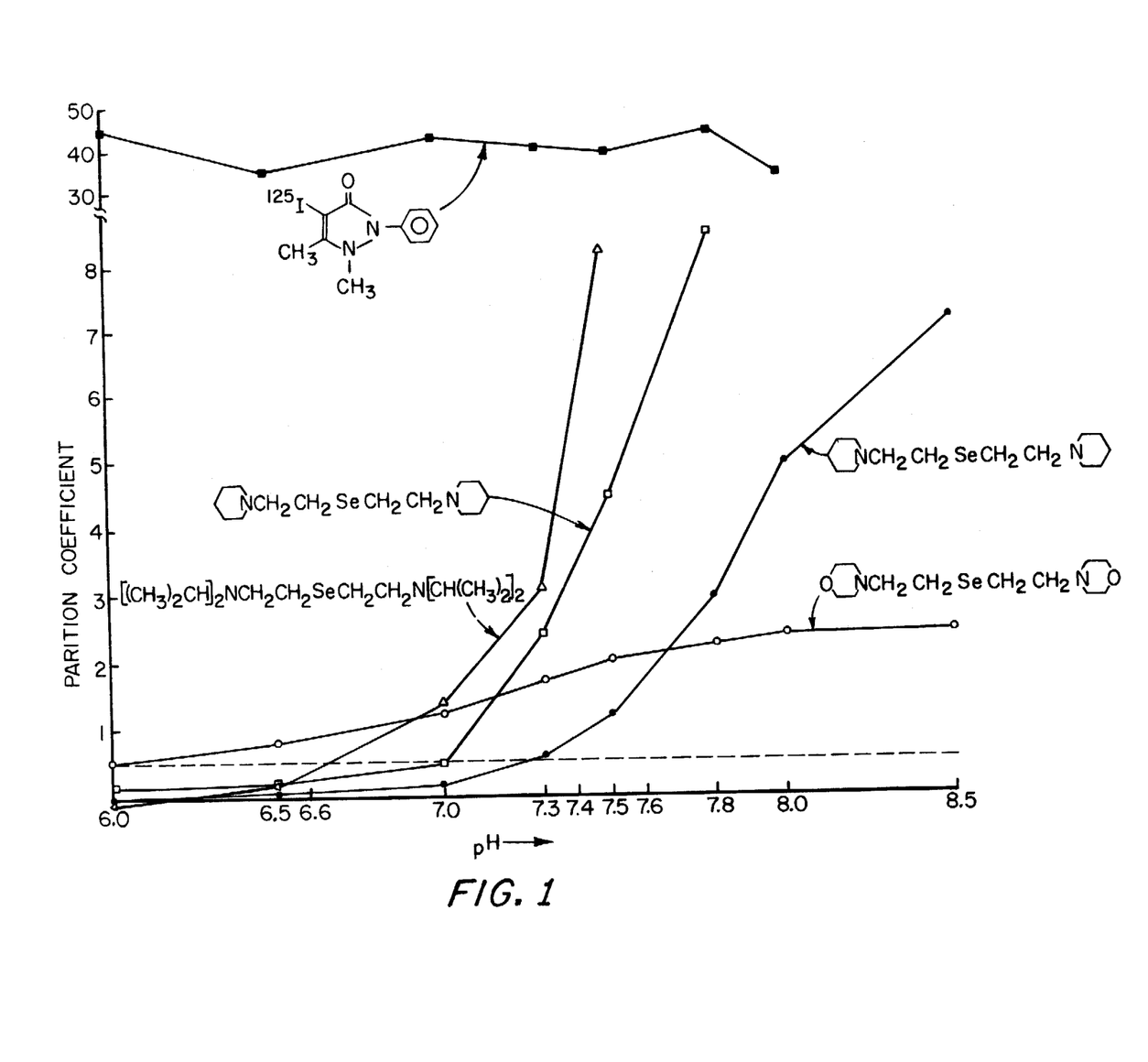
FIG. 1 is a graph showing an n-octanol-aqueous medium partition coefficient pH correlation of several compounds of the present invention, the graph also showing the partition coefficient pH correlation of iodoantipyrine.

Partition coefficients obtained in this manner for a plurality of radiopharmaceutical compounds of the present invention, are shown on the graph of FIG. 1.

It has been found that compounds which are suitable for use in the novel diagnostic method of the present invention have n-octanol-aqueous medium partition coefficients (hereinafter referred to simply as partition coefficients) which increase by at least 30% as the pH increases from 6.60 to 7.60. Preferably the partition coefficient of the compound increases by at least 100% in the pH range from 6.60 to 7.60. The preferred partition coefficient at pH 7.6 for a particular compound is often between 0.5 and 50 and is at least 23% and usually at least 50% less at pH 6.6.

It should be expressly understood that a large number of radioactive compounds may satisfy the above stated requirements and may be suitable for use in the novel diagnostic method of the present invention. Generally speaking, compounds having a γ, X-ray or positron radiation emitting isotope, at least one alkyl, cycloalkyl, arylalkyl, or arylcycloalkyl moiety and at least one and preferably at least two weakly basic groups such as a primary, secondary or tertiary amine group may be suitable for use in the novel diagnostic method of the present invention.

Radioactive isotopes suitable for use in the compounds and method of the invention, as previously discussed, emit gamma ray, X-ray or positron radiation or combinations of such emissions. The most desirable isotopes emit gamma ray or positron radiation or a combination of gamma ray and positron radiation. Gamma ray emitting isotopes as used herein means isotopes which emit gamma rays without emitting positrons. Gamma ray emitting isotopes preferably emit at least 75 numerical percent of their gamma rays at energies of between 80 and 400 kiloelectron volts and preferably between 80 and 300 kiloelectron volts.

The half life of isotopes used in accordance with the invention may be very short or very long but unless the isotope can be rapidly and almost completely eliminated from the body of the mammal being tested, the half life is preferably not longer than 15 days and most preferably not longer than 3 days. Isotopes having very short half lives cannot be used unless the isotope can be generated locally and used rapidly. In such cases the half life can be as short as 2 minutes but is usually at least 15 minutes.

As previously discussed, isotopes of iodine are not considered especially desirable both because the isotopes with desirably short half lives cannot be locally generated without prohibitively expensive high energy accelerators and because special steps must be taken to reduce or eliminate concentration of radioactive iodine in the thyroid. Such concentration in the thyroid is believed most likely when the most rapidly and easily prepared iodine containing compounds are used. Specific radioactive isotopes which are believed to be suitable for use in the compounds and method of the invention are: tellurium 123m, technetium 99m, ruthenium 97, tin 117m, lead 203, indium 111, indium 113m, gallium 67, gallium 68, scandium 44, and selenium 75.

In order to form radiopharmaceutical chemical compounds in accordance with the present invention, the selected isotope is chemically combined with at least one and preferably with at least two amine groups. Amine group as used herein includes primary, secondary and tertiary amine groups. Primary amine group as used herein means a group having a nitrogen atom chemically combined with one carbon atom and two hydrogen atoms. The carbon atom may be either an aliphatic or aromatic carbon atom. Similarly a secondary amine group means a group having a nitrogen atom combined with two carbon atoms and one hydrogen atom where the carbon atoms are either aliphatic or aromatic. A tertiary amine group is a group having a nitrogen atom chemically combined with three such carbon atoms. The carbon atoms attached to the amine nitrogen atom may be located in aliphatic or aromatic rings or may be in linear or branched chain, saturated or unsaturated, monovalent or polyvalent hydrocarbon groups. The isotope is most preferably combined with at least two tertiary amine groups. "Chemically combined" as used herein means directly combined or indirectly combined through another intermediate radical or moiety. Other radicals or moieties, whether intermediate or pendant, may be any moiety which does not adversely affect the lipophylic character of the compound, as previously discussed, and which does not increase protein binding beyond acceptable limits as will be subsequently discussed. Usually such other radicals or moieties are in the form of linear, branched, or cylic carbon chains which occasionally may include an ether or thioether linkage. Oxygen and sulfur may occasionally be present, especially to assist in the formation of chelates of metallic isotopes. The isotope in general is usually chemically bound to the balance of the compound by means of one or more covalent bonds. As used herein, "Covalent" includes the semicovalent bonds formed by chelate structures. "Chemical compound" as used herein, when referring to the compound of the invention, includes the entire compound including the radioactive isotope and all attached radicals and moieties. In general, the compound has no overall net positive charge at pH 12 and no net overall negative charge at pH 6.0. It is recognized that charge or ionization cannot always be entirely eliminated and when it is stated that the compound has no charge it is intended that less than one tenth of one numerical percent (0.1%) of the compound is in a charged form.

The weakly basic group is preferably at least one amine group and most preferably at least one tertiary amine group. The weakly basic group such as the tertiary amine group, preferably has a pKa in the range of 3.0 to 9.0. It is readily understood that as the pH of the medium increases, the compounds of the present invention, having a weakly basic moiety are gradually deprotonated and therefore assume a non-ionized lipid soluble form which is usually due to the presence of lipophilic alkyl, cycloalkyl, arylalkyl, or arylcycloalkyl groups. Lowering the pH of the medium, on the other hand, results in increasing protonation of the weakly basic group resulting in increasing hydrophilicity of the compounds. These changes are reflected by the measured partition coefficients and by behavior of the compounds in the biological systems which are described below as an integral part of the description of the present invention. In addition to the previously discussed requirements, the compounds of the present invention should have a protein binding of less than ninety percent. Compounds which are highly susceptible to protein binding are believed to become bound by blood serum and thus prevented from entering the target organ or tissue. In general, such protein binding of radiopharmaceuticals in accordance with the present invention is determined in a dual 0.5 ml chamber 1 ml dialysis cell wherein 0.5 ml of pH 7.4 phosphate buffer (0.1 M) plus radiopharmaceutical is placed in one cell and 0.5 ml of human blood plasma is placed in the remaining cell. The cells are separated by a 0.01 inch thick cellulose dialysis membrane. The cells are incubated and rotated at 37° C. for 18 hours. Samples of buffer and plasma are removed and counted to determine the percent unbound radiopharmaceutical.

It has been found in accordance with the present invention among other compounds, that a plurality of selenide compounds containing Se-75 isotope are well suited for use in the novel diagnostic method of the present invention. These selenide compounds have a general structural formula of:

First General Formula wherein Y is a divalent alkyl or cycloalkyl radical having 1–10 carbon atoms, $R_1$ is a mono-, or divalent alkyl or arylalkyl radical, $R_2$ is a mono-, or divalent alkyl or arylalkyl radical, m is an integer having the values 0 to 1, X is $CH_2$, O, S or Se and $R_3$ is an alkyl, substituted aminoalkyl, arylalkyl, cycloalkyl or arylcycloalkyl radical having 1 to 20 carbon atoms.

Other compounds for the purposes of the present invention have a second general structural formula of:

Second General Formula wherein the symbols Y, $R_1$, $R_2$, m and X have the same meaning as the symbols described above for the first general formula.

It is readily apparent from the inspection of the first and second general formulae that these compounds respectively have one or two tertiary amine moieties which are principally responsible for the desired strong dependence of the partition coefficients on the pH of an aqueous medium. Compounds of the second general formula, generally speaking, do not bear a proton on one of the tertiary amine moieties at blood pH (approximately 7.4), and the desired dependence of the compounds' lipid solubility on pH in the desired pH range is principally due to a protonation of a tertiary amine moiety.

Compounds of the first and second general formulae may be readily prepared according to a novel radiosynthetic method which comprises part of the present invention. Selenious acid ($H_2SeO_3$) containing selenium 75 label is reduced with sodium borohydride to give either sodium hydrogen selenide or disodium diselenide. As is known in the chemical arts, the product of this reduction is dependent on the amount of sodium borohydride used for the reduction. In order to obtain the symmetrical selenide compounds of the second general formula, sodium hydrogen selenide is alkylated by an alkylating agent having a general structural formula set forth herein:

Third General Formula wherein Z represents a leaving group, preferably a halogen leaving group such as chlorine, bromine, or iodine, and wherein the symbols Y, $R_1$, $R_2$, X and m have the same meaning as in the above described first and second general formulae. The alkylation with the compounds of the first general formula may be conducted in a refluxing aqueous solution in which the Se-75 labeled sodium hydrogen selenide was originally prepared.

Compounds of the second general formula may be readily obtained by alkylation of disodium diselenide as set forth above, followed by reduction of the resulting dialkyl diselenide compounds with sodium borohydride to give compounds corresponding to a fourth general formula of:

Fourth General Formula wherein W represents Na or H, and the symbols Y, $R_1$, $R_2$, X, and m have the same meaning as in the general formulae set forth above. Compounds of the fourth general formula are then readily alkylated further by an alkylating agent having the structure, $R_3$—Z wherein the symbols $R_3$ and Z have the same meaning as set forth above.

Although the intermediate compounds, Se-75 labeled sodium hydrogen selenide and Se-75 labeled disodium diselenide may also be obtained by prior art methods starting from labeled selenium metal, the above described method for the preparation of these intermediates offers a distinct advantage. This advantage lies in the fact that selenious acid ($H_2SeO_3$) may be commercially obtained at a higher specific activity than Se-75 metal. Generally speaking, the specific activities of the Se-75 labeled compounds prepared in accordance with the present invention are in the 10 microCi/mg to 1 milliCi/mg range, the yield of the radioactive compounds ranges from 30% to 70%, the radiochemical yield being generally approximately 40%.

In addition to preparing several of the Se-75 labeled compounds of the present invention, the above described synthetic method is, of course, also suitable for the preparation of corresponding non-radioactive (cold) compounds. All of the cold compounds prepared according to this method, were fully characterized by conventional analytical methodology such as infrared and proton magnetic resonance spectroscopy, and by melting points of the corresponding hydrochloride salts.

Purity of the Se-75 labeled compounds was checked by comparing their thin layer chromotography (tlc) characteristics to the tlc characteristics of the corresponding cold compounds. The thin layer chromotography solvent systems used for these comparisons were the following: chloroform, (solvent system A); methanol; water 1:1 (solvent system B); 1-butanol:acetic acid:water 4:1:2 (solvent system C), and ethylene glycol monomethylether:acetic acid:water saturated with sodium chloride 7:1.5:1.5 (solvent system D). Developed chromotograms obtained in these solvent systems were sprayed with 0.4% dipicrylamine in 50% acetone solution to give yellowish-pink spots which corresponded to the tertiary amines. After spraying, the radioactive chromotograms were cut into 0.5 centimeter pieces and the radioactivity was counted in a conventional well counter. In all cases, the radioactivity was coincident with the Rf value for the corresponding cold compound.

Table 1 shows the melting points of the dihydrochloride salts of several selected cold compounds prepared in accordance with the present invention.

Table 2 shows the chemical yield and Rf value of several selected cold compounds synthesized in accordance with the present invention. The hereinafter given specific example for the synthesis of cold di-$\beta$-(N,N-dimethylaminoethyl)-selenide dihydrochloride and for the corresponding Se-75 labeled compound is intended to serve as an illustrative example for the synthesis of the diagnostic compounds, in accordance with the present invention.

In addition to the herein described Se-75 labeled compounds, a plurality of other compounds which incorporate radionuclides as previously described may be used in the method of the present invention. Clearly, as long as the herein described criteria with regard to $\gamma$, X-ray or positron emission, lipid solubility-pH dependence, and protein binding are met, the compounds can take advantage of the regional pH shift to accomplish the herein described diagnostic purpose.

For example, tellurium 123m reacts chemically essentially identically with selenium 75 and therefore can be substituted for selenium in the previously described reactions and compounds.

Certain derivatives of ruthenocene ($C_5H_5RuC_5H_5$) are known which are believed to be modifiable to optimize lipophilicity and incorporate tertiary amine groups to obtain the required lipophylic shift within the pH range of 6.6 to 7.6. The use of the desired ruthenium 97 isotope is, of course, a simple substitution. Several publications which describe such ruthenocene compounds which are believed to be modifiable as previously described are Biochemistry of Metalocenes. The Organ Distribution of Hydroxyacetyl [$^{103}$Ru] ruthenocene and Its Glucuronide in Mice, A. J. Taylor et al, J. Nucl. Med, Vol. 21, No. 1, pp. 63–66; Biochemistry of Metalocenes. I. Distribution of $^{59}$Fe or $^{103}$Ru-Labeled Metalocene Carboxylic Acid in Mice, M. Wenzel et al., J. Nucl. Med. Vol. 18, No. 4, pp. 367–372; Derivate von [$^{103}$Ru]-Methyl-Ruthenocen Konstitution und Organ-Verteillung von Potentiellen Radiopharmaka, M. Schneider et al, J. of Labeled Compounds and Radiopharmaceuticals, Vol. XVII, No. 1, p. 1; and Darstellung von Radioaktiven Ruthenocen-Derivaten, M. Schneider et al, J. of Labeled Compounds and Radiopharmaceuticals, Vol XV, p. 295.

It is believed that certain compounds of Tin 117m are particularly suitable for use in compounds in accordance with the invention. Tin 117m can be used in compounds somewhat similar to the selenium 75 compound previously described. Examples of suggested synthesis for Tin 117m compounds suitable for use in accordance with the present invention are as follows:

(A)

where R is an organic radical which is preferably a hydrocarbon and both R and n are selected to optimize the partition coefficient in both (A) and (B) above.

Most metallic isotopes, in order to be used in compounds of the present invention, need to be in the compounds in the form of chelates. Examples of chelates of technetium 99m, which are believed to be modifiable in accordance with the present invention, to optimize the partition coefficient, to eliminate highly ionic groups such as carboxy groups and to reduce protein binding, are described in Membrane Transport of Tc-99m-Labeled Radiopharmaceuticals I. Brain Uptake by Passive Transport, M. D. Loberg et al, J. Nucl. Med. 20: pp. 1181–1188, 1979.

EXAMPLE I

Preparation of di-$\beta$-(N, N-dimethylaminoethyl)-selenide dihydrochloride

Selenious acid (0.4 g, 3.1 mmole) was dissolved in 25 ml of water. To this solution, sodium borohydride (0.5 g) was added in small portions. After heating the solution to reflux, a clear solution was obtained. N,N-dimethylaminoethyl chloride hydrochloride (0.95 g, 6.6 mmole) was added and the mixture was heated to reflux for 1 hr. The reaction mixture was then cooled to room temperature, treated with 0.4 g of sodium hydroxide and extracted with 30 ml of chloroform. The chloroform layer was separated, dried over anhydrous sodium sulfate and filtered. The filtered solution was condensed and the residue was treated with 1 ml of conc. HCl and 20 ml of abs. ethanol. After staying in a refrigerator overnight, the precipitate was filtered and the product washed with 10 ml of pet. ether. After drying, 0.52 g of the product was obtained (yield 50%).

The same procedure as that for cold compound synthesis was used for the preparation of Se-75 labeled compound. The desired amount of Se-75 labeled selenious acid was mixed with cold selenious acid and the sequence of reaction steps was performed until the point that the chloroform extract was condensed. The condensed residue was dissolved in a desired amount of saline and the solution was filtered through a 0.22 micron filter to sterilize the solution. The radiochemical purity was checked by tlc with the above described four solvent systems.

DISCUSSION OF PHYSICO-CHEMICAL PROPERTIES AND DIAGNOSTIC UTILITY OF THE COMPOUNDS OF THE PRESENT INVENTION

Figure 2:
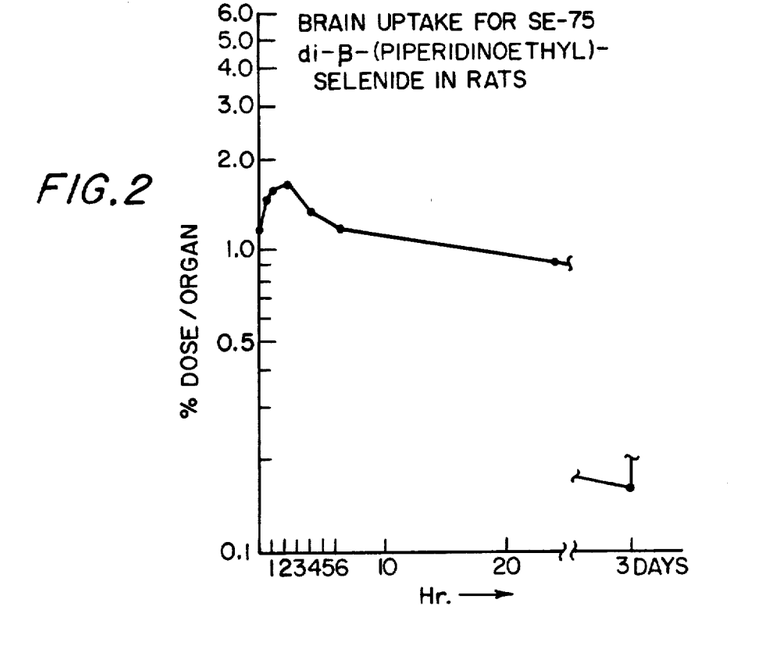
FIG. 2 is a graph showing time dependent concentration of di-$\beta$-(piperidinoethyl)-selenide in rat brains after administration of an initial dose in the bloodstream.
Figure 3:
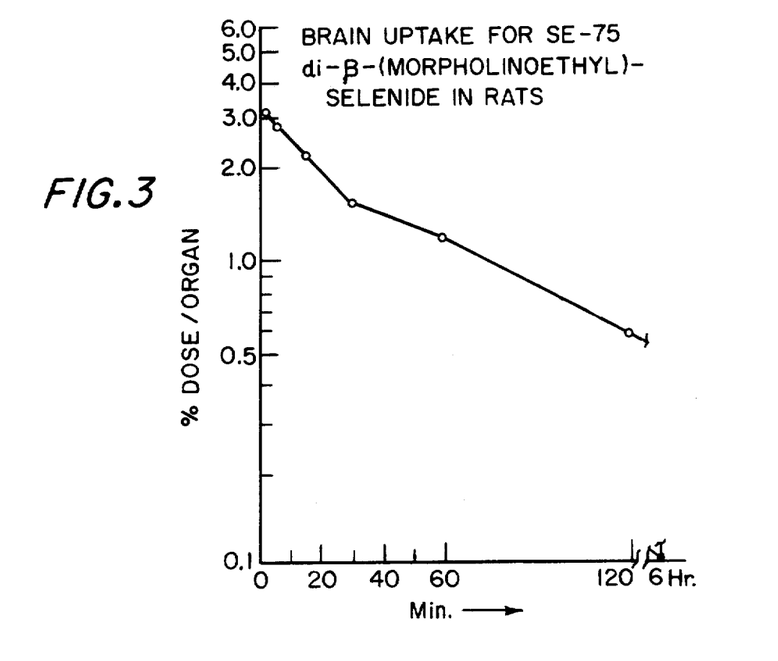
FIG. 3 is a graph showing time dependent concentration of di-$\beta$-(morpholinoethyl)-selenide in rat brains after administration of an initial dose in the bloodstream.

Referring now to the graphs of FIGS. 1 through 3 and to Tables 3 and 4, the partition coefficient-pH dependence of a plurality of compounds of the present invention as well as the distribution of two selected Se-75 labeled compounds in several organs of rats after an intravenous injection, is disclosed in detail.

Referring now more particularly to the graph of FIG. 1, measured n-octanol-aqueous medium partition coefficients of di-β-(piperidinoethyl)-selenide, di-β-(morpholinoethyl)-selenide, di-β-(N,N-isopropylaminoethyl)-selenide, di-β-(hexamethylenaminoethyl)-selenide and of di-β-(pyridylmethyl)-selenide are shown in the pH range of 6.0 to 8.5 pH units.

As is readily apparent from an inspection of FIG. 1, iodoantipyrine does not exhibit the hereinbefore described desirable changes in partition coefficient with pH changes in the region from pH 6.60–7.60. For this reason, iodoantipyrine is not suitable for use in the novel diagnostic method of the present invention. Its partition coefficient-pH dependence is shown on FIG. 1 for the sake of comparison only. Iodoantipyrine, because of its high lipid solubility, is able to penetrate brain tissue. But because there is no decrease in lipid solubility at the lower pH of the brain within one hour after penetration, iodoantipyrine almost completely leaves the brain by diffusion. Thus the behavior of iodoantipyrine is different from the remainder of the compounds in FIG. 1. The curves for each of these compounds respectively indicate that the partition coefficient changes by at least 30%, with some of the compounds changing by several hundred percent in the pH range from 6.60–7.60.

In accordance with the theory of the present invention, di-β-(morpholinoethyl)-selenide which has a higher partition coefficient at the pH of the blood (7.4) than di-β-(piperidinoethyl)-selenide and therefore higher lipid solubility, is expected to be taken up faster by various tissues and organs of the body than di-β-(piperidinoethyl)-selenide. FIGS. 2 and 3 respectively show the relative concentration of Se-75 labeled di-β-(piperidinoethyl)-selenide and di-β-(morpholinoethyl)-selenide in rat brains at several time intervals after an intravenous injection of a dose of the respective compounds into the rat. As is shown in FIG. 3, and also in Table 4, two minutes after an intravenous injection of Se-75 labeled di-β-(morpholinoethyl)-selenide, the brain uptake of the radiopharmaceutical compound reaches a value of 3.19%. In contrast, di-β-(piperidinoethyl)-selenide, shown on FIG. 2 and 3, being less lipid soluble at the pH of the blood, penetrates more slowly into the brain reaching a brain uptake of only 1.09% in two minutes after intravenous injection. The terms uptake, % uptake or % dose are used to describe the percentage of the radiopharmaceutical compound contained in a given organ or tissue as compared to the total initial dose. The numerical values in FIGS. 2 and 3 and Tables 3 and 4 represent such percentages.

Referring again to FIG. 1, it is readily apparent that although di-β-(morpholinoethyl)-selenide has a higher partition coefficient at pH 7.4 than for example di-β-(piperidinoethyl)-selenide, the latter shows a much higher partition coefficient pH dependence, particularly in the 6.6 to 7.6 range. Therefore di-β-(piperidinoethyl)-selenide is expected to be much more effectively trapped in target organs or tissues having a significant intracellular regional pH shift. An inspection of FIGS. 2 and 3 and of Tables 3 and 4 reveals that this is indeed true.

FIGS. 2 and 3 show, for example, that the brain content (% dose) of di-β-(morpholinoethyl)-selenide decreases much more rapidly after the intravenous injection than that of di-β-(piperidinoethyl)-selenide. Although the initial uptake of di-β-(morpholinoethyl)-selenide in the rat brain is higher than that of di-β-(piperdinoethyl)-selenide, 2 hours after the intravenous injection, the brain content of di-β-(piperidino-ethyl)-selenide is approximately at a peak value of 1.63% while the amount of di-β-(morpholinoethyl)-selenide in the rat brain has already declined to 0.56% (Tables 3 and 4). FIGS. 2 and 3 and Tables 3 and 4 also indicate that 6 hours after intravenous injection, the % dose of di-β-(morpholinoethyl)-selenide has already declined to a low value of 0.10%. On the other hand, the % dose of di-β-(piperidinoethyl)-selenide in the rat brain is still a very significant 1.18% 6 hours after the intravenous injection. These data indicate that desired tissue or organ penetration and retention characteristics of radiopharmaceutical compounds may be obtained in accordance with the present invention by designing compounds having predetermined partition coefficient-pH-dependence correlations.

The data of FIGS. 2 and 3 and of Tables 3 and 4 also indicate that the compounds of the present invention, as exemplified by di-β-(piperidinoethyl)-selenide and di-β-(morpholinoethyl)-selenide are capable of penetrating the blood brain barrier.

Studies of distribution of the radiopharmaceutical compounds of the present invention in rats, the results of which are reflected in FIGS. 2 and 3 and Tables 3 and 4, were conducted according to standard practice in the pharmacological sciences, and therefore need not be described here in great detail. Nevertheless, for the sake of complete understanding of the present invention, some experimental details of these studies are briefly described below:

Sprague-Dawley male rats (220–300 g) were injected intravenously (femoral vein) with a 0.2 ml solution (0.5–2 micro Ci) under light ether anaesthesia. At different time periods after the injection, the animals were sacrificed and organs of interest were excised and counted in a well counter. Percent dose was estimated by comparison of tissue counts to suitably diluted aliquots of the injected material. Total activities in blood and muscle were calculated by assuming that they are 7% and 40% of the body weight respectively.

In addition to the above described organ and tissue distribution studies in rats of the several compounds of the present invention, brain imaging studies were also conducted on rhesus monkeys using a Cleon 710 ECAT scanner.

A 5.3 kg monkey, lightly sedated with Ketalar, was injected with 1 mCi of di-β-(morpholinoethyl)-selenide, (specific activity 1 mCi/mg). Five minutes later the monkey was anaesthetized with pentabarbital. A series of tomographic images was taken at roughly ¼" intervals starting at the vertex. The first image was started 15 minutes after injection and various images were recorded up to 2 hours after injection. Each image contained approximately one million counts. At the conclusion of the imaging experiment, the monkey was killed and the brain was assayed in the dose calibrator used for measuring the injected dose. No correction was applied for the change in geometry between the syringe and the monkey brain. The weight of the brain was 84 g.

The results of the studies conducted on monkeys indicated that the distribution of di-β-(morpholinoethyl)-selenide in monkey brain resembles the distribution observed for F-18 2-fluoro-2-deoxyglucose or for N-13 labeled ammonia, with a higher uptake of the radiopharmaceutical compound in gray matter of the brain than in white matter.

It will be readily appreciated by those skilled in the pharmacological arts and particularly in nuclear medicine, that the compounds and the novel method of the present invention are readily applicable for diagnostic imaging studies in human beings also. Furthermore, such diagnostic studies are readily capable of revealing regional brain metabolism and certain other abnormal conditions such as tumors and heart disease. Application of the hereinbefore described novel diagnostic method and radiopharmaceutical compounds for diagnosing certain human diseases can be accomplished by those skilled in the art on the basis of the above teachings without undue experimentation.

TABLE I

Melting Points of Dihydrochloride Salts of Selected Cold Compounds Prepared in Accordance with the Present Invention

| STRUCTURE | MP |
|---|---|
| $(CH_3)_2-N-(CH_2)_2-Se-(CH_2)_2-N-(CH_3)_2$ | 270° C. |
| $[(CH_3)_2-CH]_2-N-(CH_2)_2-Se-(CH_2)_2-N-[CH-(CH_3)_2]_2$ | 212–215° C. |
| $O\diagup\diagdown N-(CH_2)_2-Se-(CH_2)_2-N\diagup\diagdown O$ | 203–206° C. |
| $\diagup\diagdown N-(CH_2)_2-Se-(CH_2)_2-N\diagup\diagdown$ | 238–240° C. |
| $(CH_3)_2-N-(CH_2)_3-Se-(CH_2)_3-N-(CH_3)_2$ | 180–183° C. |
| $(CH_3CH_2)_2-N-(CH_2)_2-Se-(CH_2)_2-N-(CH_2CH_3)_2$ | 206–208° C. |

TABLE 2

Chemical Yield and $R_f$ Values of Selected Cold Compounds Synthesized in Accordance with the Present Invention

| STRUCTURE | YIELDS % | A | B | C | D |
|---|---|---|---|---|---|
| $(CH_3)_2N(CH_2)_2Se(CH_2)_2N(CH_3)_2$ | 50 | 0.13 | 0.93 | 1.0 | 0.81 |
| $[(CH_3)_2CH]_2N(CH_2)_2Se(CH_2)_2N[CH(CH_3)_2]_2$ | 50 | 0–0.5 | 0.93 | 0.91 | 0.93 |
| $O\diagup\diagdown N(CH_2)_2Se(CH_2)_2N\diagup\diagdown O$ | 77 | 0.06 | 0.91 | 0.91 | 0.93 |
| $\diagup\diagdown N(CH_2)_2Se(CH_2)_2N\diagup\diagdown$ | 59 | 0–0.3 | 0.91 | 0.91 | 0.83 |

TABLE 3

ORGAN DISTRIBUTION SE-75 LABELED DI-β-(PIPERIDINOETHYL)-SELENIDE IN RATS AFTER INTRAVENOUS INJECTION % DOSE/ORGAN, AVERAGE OF 3 RATS

| TIME | 2 min | 30 min | 1 hr | 2 hr | 4 hr | 6 hr | 24 hr | 3 day |
|---|---|---|---|---|---|---|---|---|
| BLOOD | 4.58 | 0.87 | 0.75 | 0.65 | 0.59 | 0.51 | 0.20 | 0.08 |
| MUSCLE | 7.39 | 13.4 | 16.1 | 12.0 | 11.9 | 11.5 | 2.81 | 0.40 |
| HEART | 3.04 | 0.89 | 0.35 | 0.19 | 0.16 | — | 0.03 | — |
| LUNG(2) | 20.0 | 2.83 | 1.92 | 0.85 | 0.82 | — | 0.31 | — |
| PANCREAS | 0.62 | 1.42 | 1.07 | 0.84 | 0.60 | — | 0.11 | — |
| SPLEEN | 0.51 | 1.31 | 0.90 | 1.03 | 0.61 | 0.34 | 0.10 | 0.01 |
| LIVER | 12.0 | 14.3 | 16.6 | 15.9 | 16.0 | 7.66 | 4.79 | 1.72 |
| KIDNEY | 7.14 | 9.21 | 4.43 | 2.89 | 1.53 | 0.64 | 0.38 | 0.12 |
| BRAIN | 1.09 | 1.49 | 1.53 | 1.63 | 1.32 | 1.18 | 0.91 | 0.16 |

TABLE 4

ORGAN DISTRIBUTION OF SE-75 LABELED DI-β-(MORPHOLINOETHYL)-SELENIDE AFTER INTRAVENOUS INJECTION % DOSE/ORGAN, AVERAGE OF 3–6 RATS**

| TIME | 2 min | 5 min | 15 min | 30 min | 1 hr | 2 hr | 6 hr | 24 hr |
|---|---|---|---|---|---|---|---|---|
| BLOOD | 3.13 | 2.72 | 2.26 | 2.82 | 2.61 | 2.46 | 0.61 | 0.13 |
| MUSCLE | 10.5 | 15.0 | 19.4 | 14.4 | 13.6 | 17.7 | 3.43 | 0.74 |
| HEART | 0.45 | — | — | 0.22 | — | 0.18 | — | 0.02 |
| LUNG(2) | 2.77 | — | — | 1.79 | — | 0.94 | — | 0.04 |
| PANCREAS | 0.88 | — | — | 0.38 | — | 0.25 | — | 0.01 |
| SPLEEN | 0.68 | 0.87 | 1.23 | 1.55 | — | 0.88 | 0.19 | 0.10 |
| LIVER | 18.3 | 19.7 | 22.1 | 23.3 | 29.9 | 21.7 | 4.38 | 2.15 |
| KIDNEY(2) | 9.89 | 7.46 | 4.04 | 4.03 | 4.30 | 3.42 | 0.64 | 0.29 |
| BRAIN | 3.19* | 2.80 | 2.23 | 1.53 | 1.19 | 0.56 | 0.10 | 0.02 |

*Average of 5 samples
**Average of 6 rats

We claim:

1. A method for selectively depositing a radiopharmaceutical compound emitting radiation readily observable by radiation detecting means in at least one target tissue or organ of a mammal, the target tissue or organ having a physiologically significantly different intracellular pH than the blood of the mammal, the method comprising the step of:
   introducing a radiopharmaceutical compound, containing a radioactive isotope other than an isotope of iodine, into the bloodstream of the mammal, the compound having such acid-base characteristics that a state of ionization of the compound at the pH of the blood of the mammal is significantly different than its state of ionization at the intracellular pH of the target tissue or organ, the compound having such lipid solubility characteristics that the compound is capable of ready penetration through cell walls of the target tissue or organ wherein due to a change in its state of ionization, its lipid solubility is substantially decreased whereby an ability of the compound to exit from the target tissue or organ is substantially diminished so that the compound is at least temporarily trapped within the target tissue or organ; said compound having at least a 30% positive change in its n-octanol-aqueous medium partition coefficient at a pH change of from 6.60 to 7.60 pH units and containing at least one amine group.

2. The method of claim 1 wherein the compound contains at least one amine group.

3. The method of claim 1 wherein the compound is a weak organic base and has a percent protein binding of less than ninety percent.

4. The invention of claim 3 wherein the partition coefficient of the compound has a positive charge of at least 100% in the range of 6.60 to 7.60 pH units.

5. The method of claim 1 wherein the compound is a ditertiary amine or a physiologically acceptable salt thereof, the ditertiary amine including at least one moiety having a radioactive element emitting $\gamma$, X-ray or positron radiation.

6. The method of claim 1 wherein the compound has the generic formula of:

wherein
Y is a bivalent alkyl radical of up to 3 carbon atoms,
$R_1$ is an alkyl radical of up to 3 carbon atoms.
$R_2$ is an alkyl radical of up to 3 carbon atoms and
$R_3$ is an alkyl, substituted aminoalkyl, arylalkyl, cycloalkyl, or arylcycloalkyl radical of from 1 to 20 carbon atoms.

7. The method of claim 1 wherein the compound has the formula of:

wherein
n is an integer having the values of 1-10,
$R_1$ is a mono or divalent alkyl radical of up to 3 carbon atoms,
$R_2$ is a mono or divalent alkyl radical of up to 3 carbon atoms,
m is an integer having the values of 0 or 1,
x is independently at each occurrence $-CH_2-$, O, S or Se and
$R_3$ is an alkyl substituted aminoalkyl, arylalkyl, cycloalkyl, or arylcycloalkyl radical of from 1 to 20 carbon atoms.

8. The method of claim 1 wherein the compound has the formula:

wherein
Y is independently at each occurrence a bivalent alkyl radical of up to 3 carbon atoms,
$R_1$ is independently at each occurrence an alkyl radical of up to 3 carbon atoms, and
$R_2$ is independently at each occurrence an alkyl radical of up to 3 carbon atoms.

9. The method of claim 1 wherein the radiopharmaceutical compound has the formula of:

wherein
n is an integer having the values 1-10,
$R_1$ is independently at each occurrence a mono or divalent alkyl radical of up to 3 carbon atoms,
$R_2$ is independently at each occurrence a mono or divalent alkyl radical of up to 3 carbon atoms,
m is an integer having the values 0 or 1, and
X is independently at each occurrence $-CH_2-$, O, S or Se.

10. The method of claim 9 wherein:
n equals 2,
$R_1$ is $-CH_2-CH_2-$,
$R_2$ is $-CH_2-CH_2-$,
m equals 1, and
X is $-CH_2-$.

11. The method of claim 9 wherein:
n equals 2,
$R_1$ is $-CH_2-CH_2-$,
$R_2$ is $-CH_2-CH_2-$,
m equals 1, and
X is $-O-$.

12. A radiopharmaceutical method for observing at least one target tissue or organ of a mammal, the target tissue or organ having a physiologically significantly lower intracellular pH than the blood of the mammal, the method comprising the steps of:
introducing a radiopharmaceutical compound into the bloodstream of the mammal, the compound containing at least one radioactive element, other than an isotope of iodine, emitting $\gamma$, X-ray or positron radiation detectable by radiation detecting means, the compound having a n-octanol-aqueous medium partition coefficient which is significantly dependent on pH of the aqueous medium at least in the pH range of 6.6 to 7.6 so that the n-octanol-aqueous medium partition coefficient of the compound increases with increasing pH at least in said pH range; said compound containing at least one amine group;
allowing the compound to penetrate into cells of the target tissue or organ by diffusion through the cell membranes wherein due to the lower pH, the n-octanol-aqueous medium partition coefficient of the compound is significantly diminished whereby a rate of exit of the compound from the target tissue or organ by diffusion is significantly diminished compared to its rate of entry into the target tissue or organ, resulting in at least temporary accumulation of the compound in the target tissue or organ; and detecting with a radiation detecting means the accumulated compound in the target tissue or organ.

13. The method of claim 12 wherein the compound is a weak organic base having at least one pKa in the range of 3.0–9.00.

14. The method of claim 12 wherein the compound is a selenide containing Se-75 isotope and at least one tertiary amine moiety.

15. The method of claim 12 wherein the target organ is the brain of the mammal.

16. The method of claim 12 wherein the target tissue is a tumor tissue.

17. The method of claim 12 wherein the target tissue is heart tissue.

18. The method of claim 12 wherein the target tissue is an abscess.

19. The method of claim 16 or 17 wherein the compound has the formula:

wherein
  n is an integer having the values 1–10,
  $R_1$ is independently at each occurrence a mono or divalent alkyl radical of up to 3 carbon atoms,
  $R_2$ is independently at each occurrence a mono or divalent alkyl radical of up to 3 carbon atoms,
  m is an integer having the values 0 or 1, and
  X is independently at each occurrence $-CH_2-$, O, S or Se.

20. The method of claim 19 wherein
  n equals 2,
  $R_1$ is $-CH_2-CH_2-$,
  $R_2$ is $-CH_2-CH_2-$,
  m equals 1, and
  X is $-CH_2-$.

21. The method of claim 20 wherein
  n equals 2
  $R_1$ is $-CH_2-CH_2-$,
  $R_2$ is $-CH_2-CH_2-$,
  m equals 1, and
  X is $-O-$.

* * * * *